(12) United States Patent
Brotz

(10) Patent No.: US 6,270,517 B1
(45) Date of Patent: Aug. 7, 2001

(54) SUTURE ASSEMBLY AND METHOD

(76) Inventor: Gregory R. Brotz, P.O. Box 1322, Sheboygan, WI (US) 53081

(*) Notice: Subject to any disclaimer, the term of this patent is extended or adjusted under 35 U.S.C. 154(b) by 0 days.

(21) Appl. No.: 09/498,307

(22) Filed: Feb. 4, 2000

(51) Int. Cl.[7] ................................................. A61B 17/00
(52) U.S. Cl. ........................ 606/228; 606/215; 606/230
(58) Field of Search .................................. 606/213, 214, 606/215, 216, 224, 228, 230, 232

(56) References Cited

U.S. PATENT DOCUMENTS

| | | | | |
|---|---|---|---|---|
| 4,261,244 | * | 4/1981 | Becht et al. | 411/472 |
| 4,467,805 | * | 8/1984 | Fukuda | 128/334 |
| 4,526,173 | * | 7/1985 | Sheehan | 128/335 |
| 5,425,747 | * | 6/1995 | Brotz | 606/228 |
| 5,441,059 | * | 8/1995 | Dannan | 128/898 |
| 5,584,859 | * | 12/1996 | Brotz | 606/228 |
| 5,906,617 | * | 5/1999 | Meislin | 606/72 |
| 6,096,074 | * | 8/2000 | Pedros | 623/2 |

* cited by examiner

Primary Examiner—Cary E. O'Connor
(74) Attorney, Agent, or Firm—William Nitkin

(57) ABSTRACT

A suture assembly made of bioabsorbable material is disclosed having a central body member with a plurality of elongated lateral members extending therefrom, each lateral member having body tissue retention means such as provided from a plurality of barb members extending at an acute angle therefrom and/or an adhesive disposed thereon. The lateral members are inserted laterally into the two sides of a cut in body tissue, such lateral members each drawn into place, in one embodiment, by its attached thread member which is connected to a needle member at the end thereof. Also disclosed is a method for utilizing the suture assembly of this invention.

7 Claims, 7 Drawing Sheets

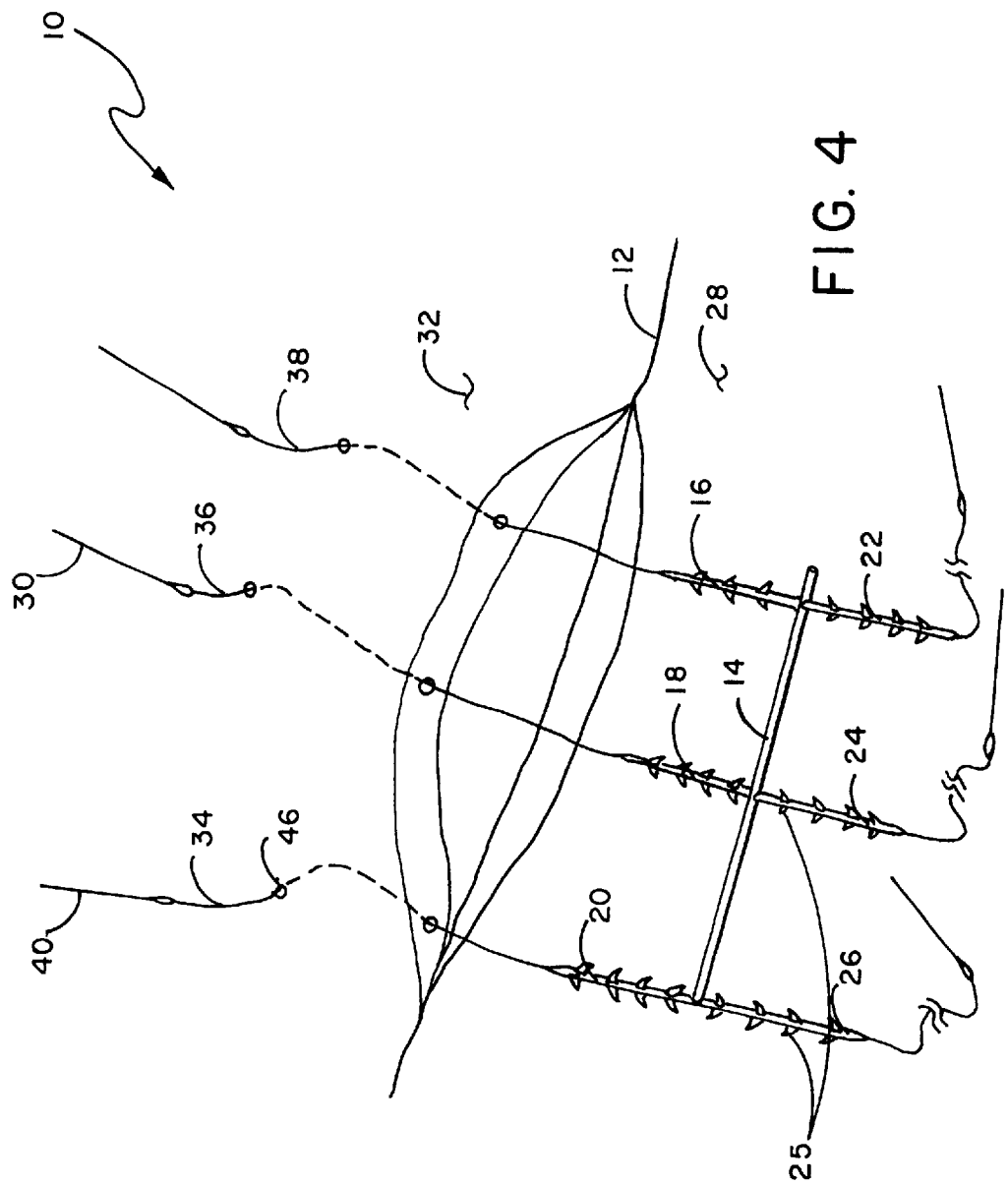

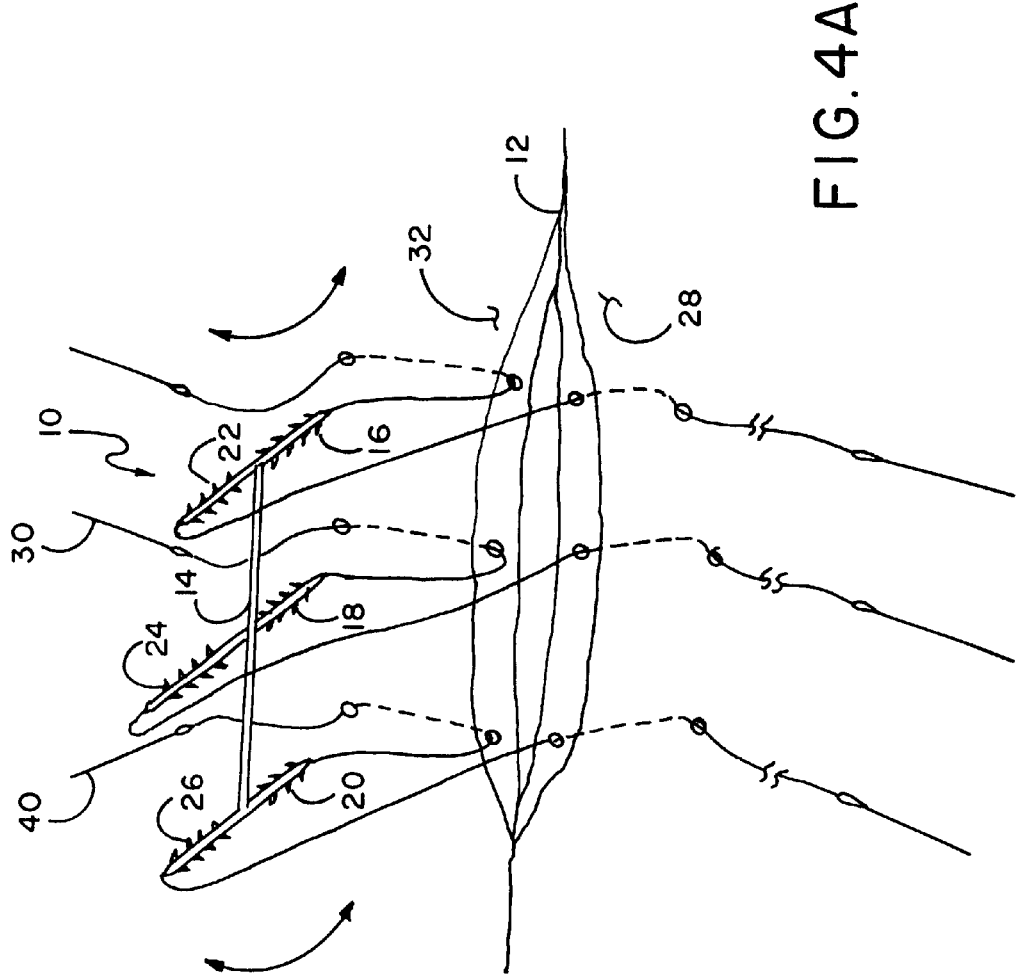

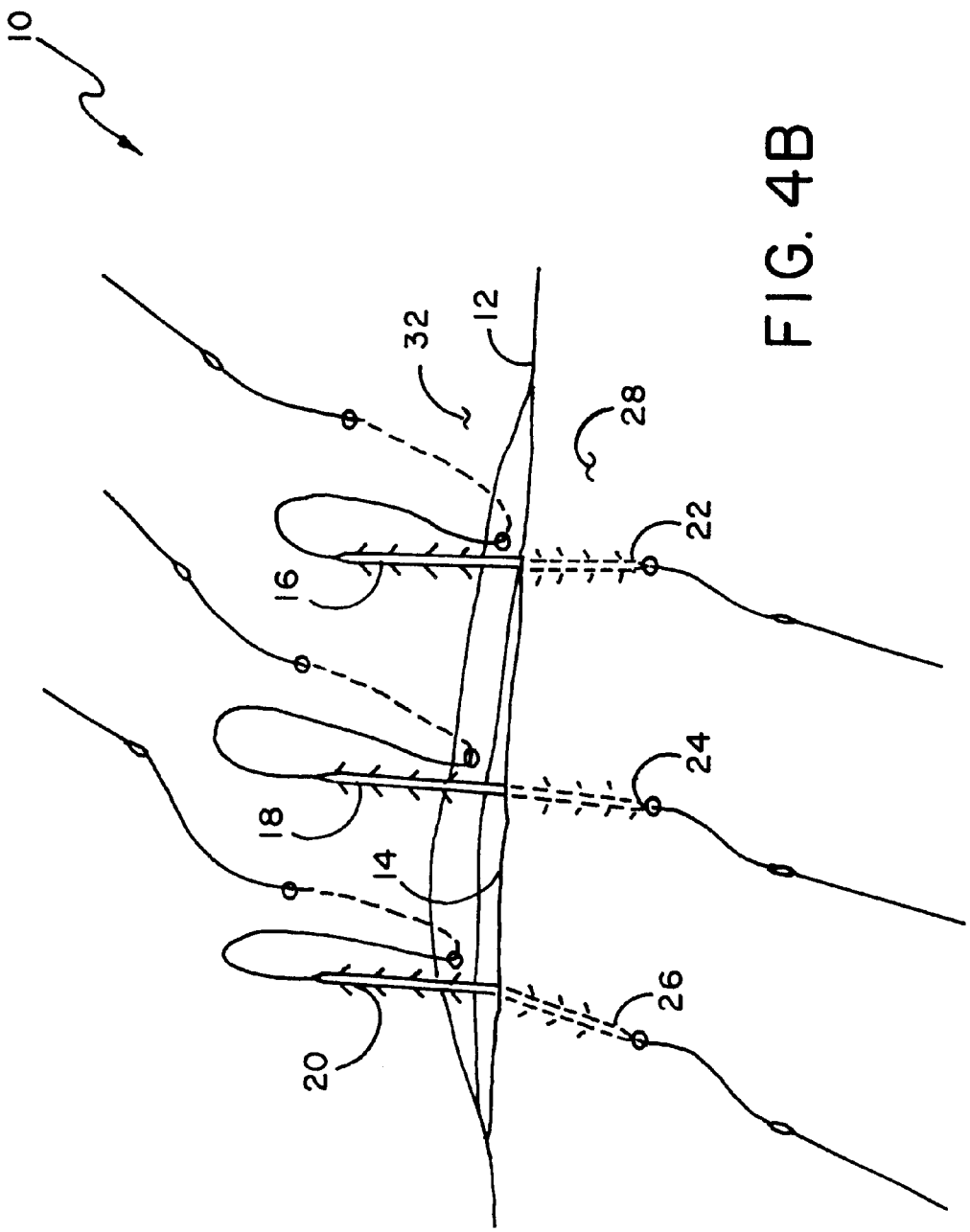

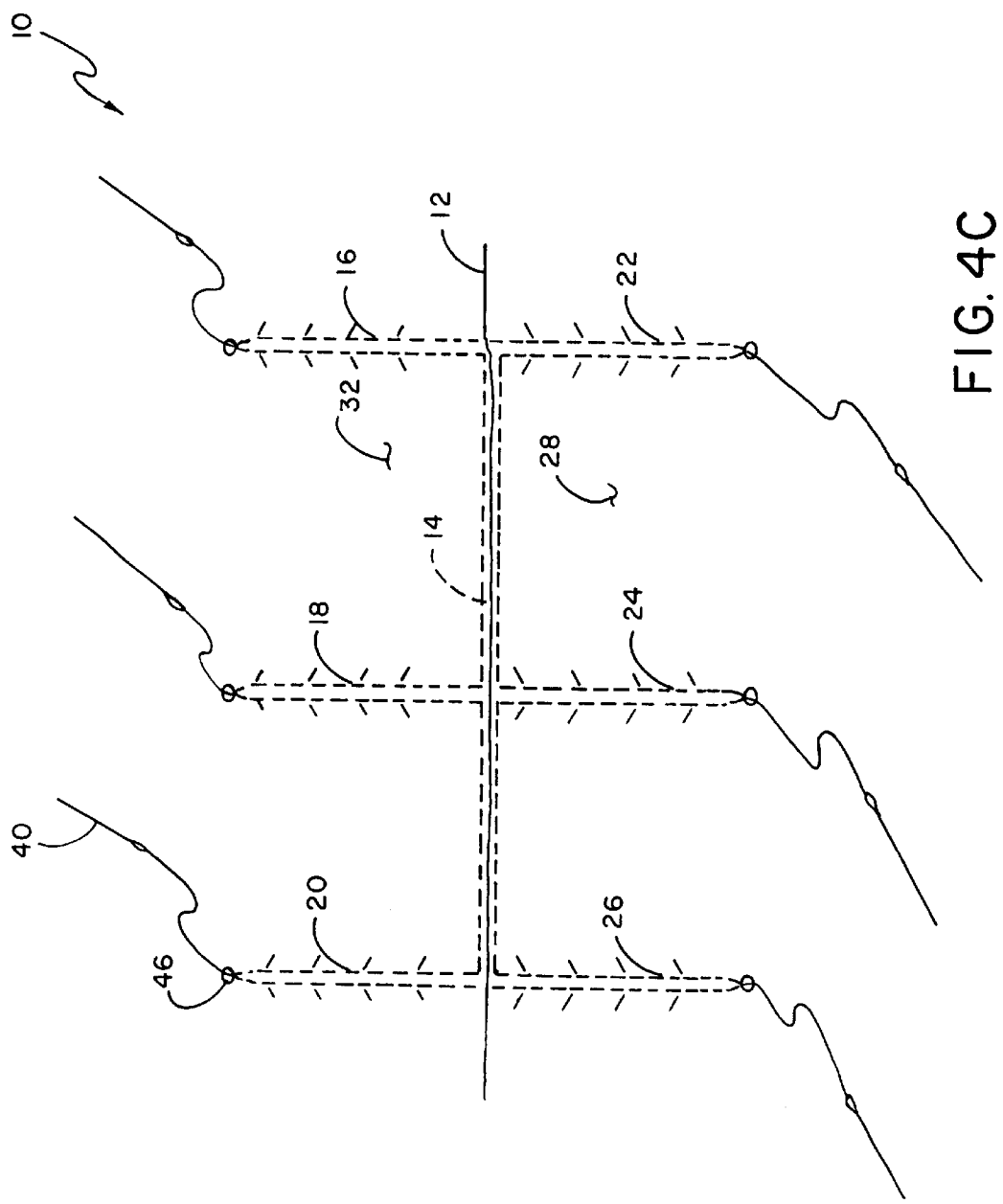

SUTURE ASSEMBLY AND METHOD

BACKGROUND OF THE INVENTION

1. Field of the Invention

The device of this invention resides in the area of sutures and fasteners for closing the two sides of an incision or cut in human skin or other body tissue and more particularly relates to a device having a central body member from which extend a plurality of lateral members with skin retention means, such as multiple barb members formed thereon or adhesive, which lateral members are pulled laterally into the two sides of a cut or incision to join the two sides of the cut together around the central body member.

2. Description of the Prior Art

Sutures for closing incisions or wounds are well known in the prior art. Such sutures or ligatures are often attached to the shank end of a needle and are utilized by physicians to make stitches to close incisions or wounds so that they may heal. Sutures are formed not only of threadlike material, but are also available as a one-piece unit combined with a needle. Sutures are available in a wide variety of monofilament and braided suture material. Sutures can be formed of non-absorbable material such as cat gut, silk, nylon, polyester, polypropylene, linen, or cotton as well as bioabsorbable synthetic material such as polymers and copolymers of glycolic and lactic acid. Germicides can also be incorporated into the structure or sutures which can be retained by the suture substrate to provide long-lasting germicidal properties.

Also known in the prior art are fasteners which eliminate the need for sutures in many instances. These fasteners are commonly referred to as "staples" and are useful in joining tissue layers laterally, for example, closing wounds in skin or fascia. Such staples are dispensed by implanting devices loaded with such surgical fasteners, the use of which devices can accomplish in very short time what would take many minutes to perform by suturing. Some staples can be made of bioabsorbable materials. The use of such fasteners results in a significantly reduced loss of blood and also lowers the level of trauma to the patient. Such staples can be in the form of metal staples which have arms bent by the fastening device to hook the separated body tissue together. Staples can require the stapling apparatus to have an anvil member which must be positioned under the tissue to be stapled so that the arms of the staple can be bent inwards. Two-part fastening devices also have been used which incorporate a barbed staple, the arms of which are attached to a bottom retaining member. One drawback to employing staples requiring that a retainer member be attached to it is that there must be means for positioning such retainer member under the body tissue to be joined, and one must have access to the body tissue both from above and below the body tissue. Metal staples applied to the body must also be removed by staple extractors.

Other types of surgical fasteners include skin tacks which are used to join two sides of an incision. Such skin tacks include a barbed tip on each end of the inverted U-shaped tack, the body of which is transversely positioned across an incision or cut and the tack applied so that the barbed tips engage straight downward into the skin to hold each side of the adjacent layers of body tissue together. More recently "zippers" have been applied on each side of an incision which allow for reopening, if desired.

Applicant has invented a suture assembly having a central body member with a plurality of elongated lateral members extending from the central body member from each side thereof, each such lateral member having a plurality of barbs thereon to retain the lateral members securely in the body tissue, as described in U.S. Pat. No. 5,425,747. Applicant further developed a method of lateral member insertion utilizing shaft-like, removable insertion members which can push each lateral member into position in the tissue and which insertion member can then be removed, as described in Applicant's U.S. Pat. No. 5,584,859.

SUMMARY OF THE INVENTION

It is an object of this invention to provide an improved surgical fastener for joining skin or other body tissue such as separated by a cut or an incision.

The structure of this invention consists of a central body member having first and second sides and first and second ends and having a plurality of lateral members attached thereto, such lateral members having an inner end, an outer end, and a length and being disposed in one embodiment in the same plane parallel to one another and perpendicular to the central body member. In one embodiment disposed on the outer end of each lateral member is a plurality of barb members, each of which extend therefrom at a rearwardly disposed acute angle to the direction of insertion. These lateral members, when inserted laterally into the skin or body tissue, remain fixed in position because the barb members, if the skin or body tissue is moved in a direction away from the central body member, will catch the skin or body tissue and prevent such outward movement. In another embodiment adhesive can be used to hold the lateral members in position instead of, or in addition to, the barb members. In a further embodiment, in order to aid in inserting the lateral members, each lateral member can have its pointed end attached to a thread member extending to a needle member. To insert a lateral member, the needle member is manually inserted into the tissue in one side of the cut at an insertion point, pushed through the tissue a distance longer than the length of the lateral member and then directed out of the tissue at an exit point such that as the needle member pulls the thread member, it pulls the attached lateral member into the tissue where the barb members, if used, allow it to advance as they are rearwardly facing. When the lateral member has reached its desired position, the user ceases pulling on the needle member and thread member and cuts off the thread member at the exit point on the surface of the skin. This procedure is done for each lateral member until they are all in the desired position, closing the cut on each side around the central body member. If an adhesive coating is used instead of barb members, the needle and thread are held in position until the adhesive has bonded to the tissue. The structure of the suture assembly and thread members of this invention can be made of bioabsorbable material so that they will dissolve gradually as the cut or incision heals. Surgical adhesives based on collagen, fibrinogen or other thrombin/fibrinogen glue formulations can be used in various coating configurations with the suture assembly of this invention. When using adhesive coatings rather than barb members to retain the suture assembly in place, it should be noted that the adhesive formulations can be placed on the lateral members. When a lateral member with such adhesive coating is inserted into the body tissue, moisture on the tissue can have a solvating effect on the glue components which become mixed together as the lateral member passes through the tissue. In order to better retain the adhesive thereto, the suture surface can be modified by ion treatments or chemical surface activating agents. The lateral members can also be physically pitted or cratered to provide stronger bonding of the adhesive thereto to prevent the suture from unintentionally releasing its adhesion to the body tissue. The lateral members and central body member can have an extremely narrow diameter, yet be stiff enough to be pulled into the skin or other tissue to be joined. The structure material can not only be round, as illustrated, but also can be flat, oval or other cross-sectional shape including being hollow and containing material. The barb members can be disposed either in a plane parallel to the plane of the lateral members or, in an alternate embodiment, can be disposed not only parallelly but also perpendicularly to such plane or at other positions around the lateral members to provide for even greater retention of the suture assembly within the skin or body tissue into which the lateral members of the suture assembly of this invention are inserted. In some embodiments the central member can be short or extremely small, and the lateral members can extend at various angles therefrom and are not necessarily parallel to one another. In other embodiments only a single, straight or bent member can be used. When a single lateral member is used, each side thereof can be treated with adhesive and the suture advanced subcutaneously from an insertion point on one side of the cut, drawn across the cut or incision so that its midpoint is located at such cut or incision, entered into the other side of the cut and drawn out an exit point with the sides of such cut or incision thereby held together by such suture.

BRIEF DESCRIPTION OF THE DRAWINGS

FIG. 4 illustrates a perspective view showing the first step of the installation of the suture of this invention into a cut.

FIG. 4A illustrates a perspective view showing the second step of the installation of the suture of this invention into a cut.

FIG. 4B illustrates a perspective view showing the third step of the installation of the suture of this invention into a cut.

FIG. 4C illustrates a perspective view showing the fourth step of the installation of the suture of this invention into a cut.

DESCRIPTION OF THE PREFERRED EMBODIMENT(S)

Figure 1:
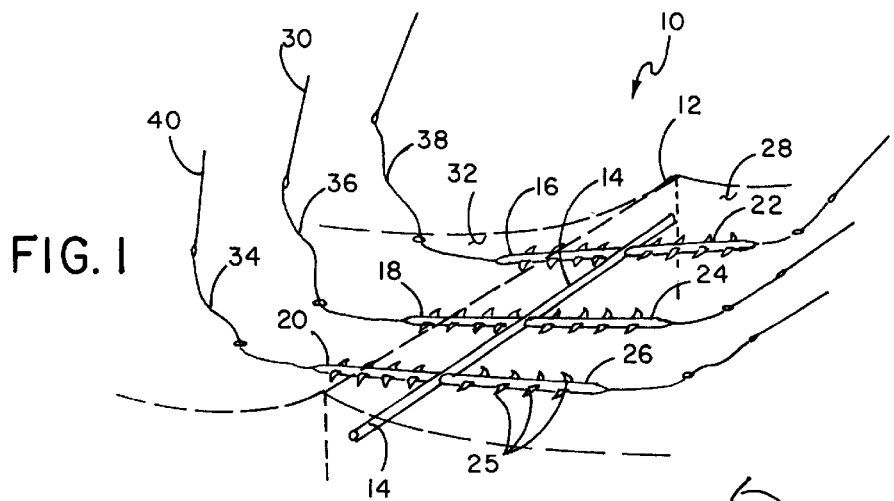
FIG. 1 illustrates a perspective view of one embodiment of the suture assembly of this invention showing it in position holding the sides of a cut together.
Figure 2:
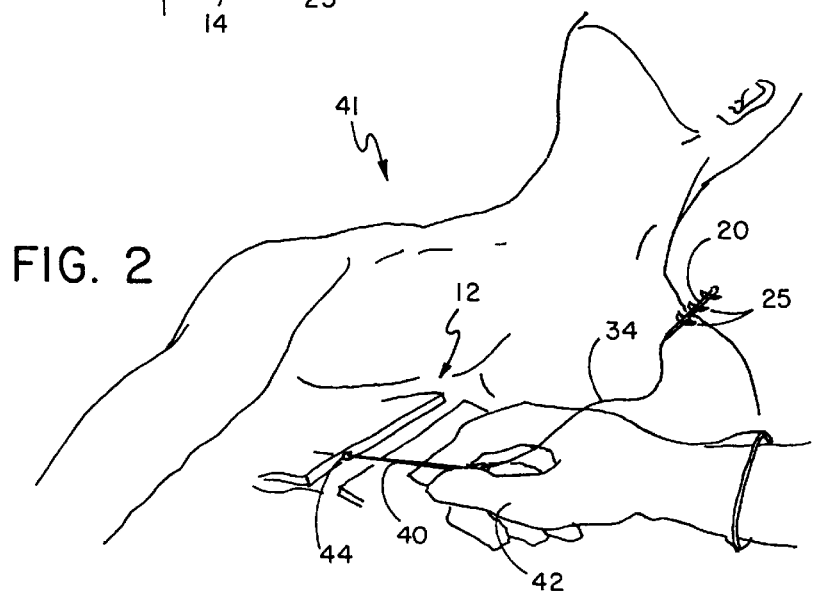
FIG. 2 illustrates a perspective view of one of the needle members being inserted into one side of a cut.
Figure 3:
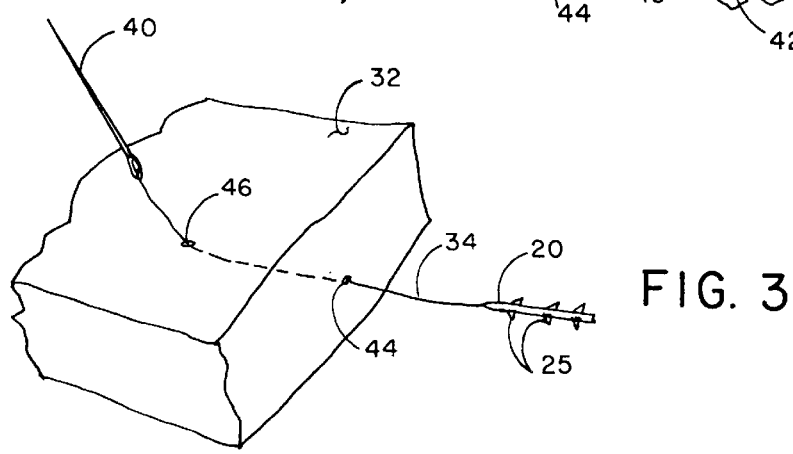
FIG. 3 illustrates an enlarged perspective view of one lateral member about to be pulled into one side of a cut.

FIG. 1 illustrates a perspective view of one embodiment of suture assembly 10 of this invention with a plurality of substantially parallel lateral members 16, 18, 20, 22, 24 and 26, each in substantially planar relationship to one another, each of said lateral members having an inner end connected substantially perpendicular to central body member 14. The suture assembly is positioned within cut 12 so that central body member 14 and the lateral members are not disposed on the surface of the skin which positioning might otherwise obstruct the adherence of any bandage placed over cut 12 or prevent the two sides of the cut from touching. If one needs to remove the suture assembly, one can cut along the original incision and cut off the lateral members and push out the lateral members in the direction of insertion. One can also pull such lateral members out by their attached thread, or one can leave the lateral members in place until they dissolve. The tips of each of the lateral members are pointed to aid in their easy insertion into the body tissue. Attached to the outer end of each lateral member or formed contiguously therewith is a thread member, for example thread member 34 attached to lateral member 20; thread member 36 attached to lateral member 18; and thread member 38 attached to lateral member 16. The thread members can be made of bioabsorbable material similar to that of the rest of the suture structure. Attached to the other end of each thread member is a needle member, such as needle member 30 attached at its shank to thread member 36; and needle member 40 attached at its shank to thread member 34. In use as seen in FIG. 2, the needle member is held by the user's hand, such as needle member 40 held by user 42 and shown being inserted into patient 41. Needle member 40 can be straight or curved and is inserted into one side of the cut at insertion point 44 and is drawn through the tissue, as seen in FIG. 3, to be pulled out at exit point 46 within side 32 of the cut. The needle member is then pulled, drawing thread member 34 through the cut from insertion point 44 to where it passes through exit point 46 and thereby drawing lateral member 20 into the tissue where it advances but cannot be retracted therefrom because of barbs 25 catching on the tissue. FIG. 4 illustrates that all the needle and thread members, such as needle member 40 and thread member 34 and needle member 30 and thread member 36 and all the other needle/thread member combinations can be inserted through a side of cut 12 and pulled out of their respective exit points, such as needle 40 pulled out of exit point 46. The suture assembly can be seen lying on side 28 of cut 12. At this point in the installation, as seen in FIG. 4A, the suture can be moved over to side 32 of the cut and the needle and thread combinations at the ends of lateral members 22, 24 and 26 can be inserted into the appropriate side of cut 12 and pulled out of their respective exit points in side 28 of cut 12. At this point in the installation, as seen in FIG. 4B, the needle and thread members at the ends of lateral members 22, 24 and 26 can be pulled, thereby pulling lateral members 22, 24 and 26 into side 28 of cut 12. Lastly, as seen in FIG. 4C, the needle and thread members attached to lateral members 16, 18 and 20 can be pulled so as to cause lateral members 16, 18 and 20 to be pulled into side 32 of cut 12 such that the sides of cut 12 are then positioned around central body member 14. When all of the needle members have been respectively inserted into their respective sides of cut 12 and pulled so that the lateral members are embedded within both sides of the cut such that the sides of the cut surround central body member 14, as seen in FIG. 4C, the thread members can be cut off at their respective exit points, and the suture assembly of this invention is then installed.

Although a surgical incision is illustrated in the Figures, the suture assembly of this invention can also be used to fasten the irregular sides of a cut or accidental wound. The central body member can be flexible to bend to accommodate any irregularities in the shape of the cut or it can be very short with the lateral members extending at angles therefrom. The suture of this invention is shown substantially enlarged in these views, but its size can vary depending on several factors such as the extent of the cut, the type of body tissue to be joined, the location of the cut, etc. The suture assembly can be made of bioabsorbable material which is well known in the prior art and should have sufficient stiffness so as to be able to be laterally pulled into the skin or body tissue. The lateral members can have flexibility as long as the barbs are rigid and the lateral members do not stretch. The central body member can also have flexibility. Surgical adhesives can be used to hold the lateral members in position and in closure of the cut or incision. In all embodiments of the suture assembly of this invention, the central body member and lateral members can be of any desired length. The central body member can be packaged in a variety of precut lengths. As seen in FIG. 1, central body member 14 has a plurality of laterally extending lateral members, such as lateral members 16, 18, 20, 22, 24 and 26 although it should be noted that any number of lateral members can be utilized. Barb members 25 can be either molded in a barb-like shape or can be formed from acute angular cuts made directly in the bioabsorbable material of the lateral members with such cut portions pushed outward and separated away from the lateral member. The barb members, in one embodiment, can be formed parallel to the plane of the lateral members. The shaft of the lateral members and the central body member in a preferred embodiment can be round in cross-section but also can be of other shapes, as discussed above.

Figure 5:
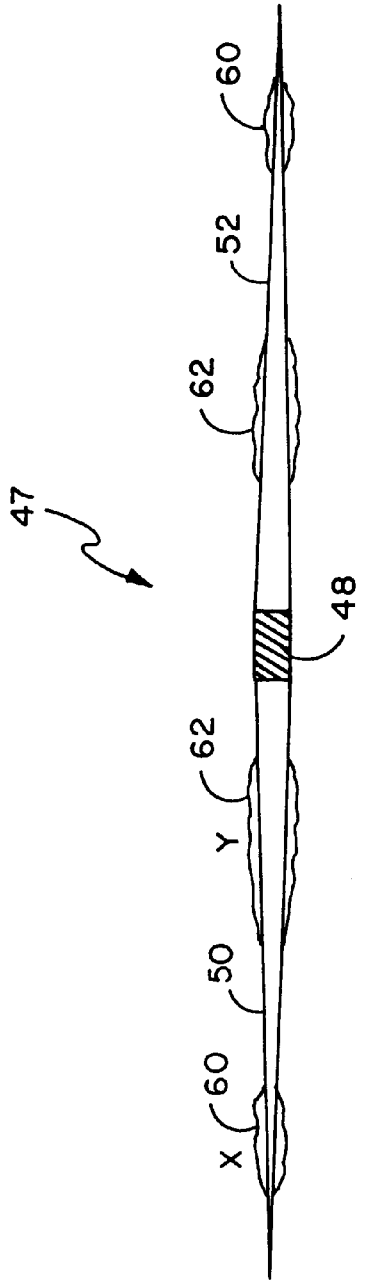
FIG. 5 illustrates a side view of a single suture member with coatings thereon that mix when inserted into the tissue to activate the adhesive nature of such coatings.
Figure 5A:
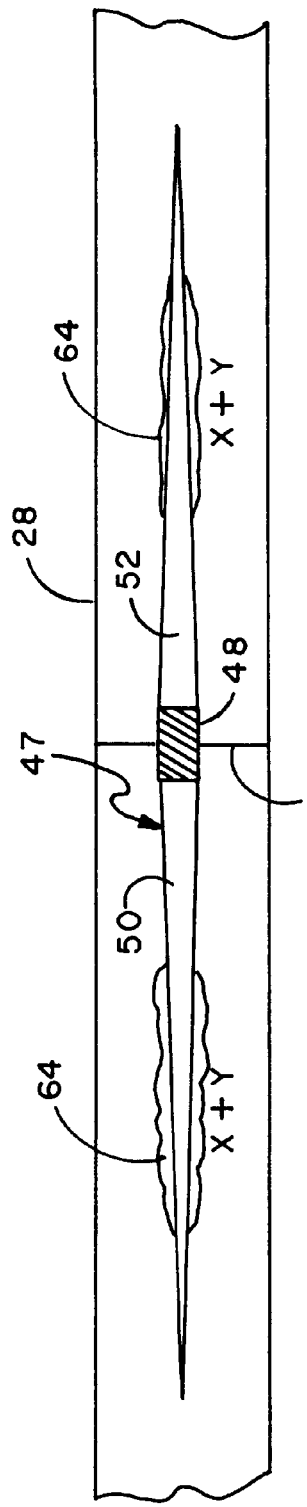
FIG. 5A illustrates a side cross-sectional view of the single suture of FIG. 5 inserted into tissue with the adhesive coatings mixed together.

In yet another embodiment the suture assembly of this invention can be made of a single piece of material, as seen in FIG. 5, having a central junction area 48 which can be disposed at the incision, with first lateral side 50 inserted into first side of the incision and second lateral side 52 inserted into the other side of the incision, as seen in FIG. 5A. The one-piece structure of this invention, as seen in FIG. 5, can be held in place by barb members, as described above, and pulled into place by attached needles and threads at each end thereof or pushed into place, as described in my previous Pat. No. 5,584,859. In the embodiment illustrated in FIG. 5, the suture member is held in place by adhesive instead of barb members which can be coated thereon. In some embodiments the adhesive can be a two-part adhesive with one part X disposed on the outer portion of a lateral side and the second part Y disposed on an inner portion of the lateral side closer to the central junction such that as the lateral side moves into the tissue, the adhesive on its outer portion is forced by the body tissue toward the central junction and mixes with the second part of the adhesive on the inner portion of that side which mixing causes the adhesive to be activated, thereby adhering the lateral side within the body tissue. As seen in FIG. 5, a dry or gel-phase thrombin 60 can be coated onto the outer portion of each lateral side and a dry or gel-phase fibrinogen 62 can be coated onto the inner side of each lateral member. As the lateral member is inserted into the body tissue, the moisture present in the body tissue solvates the thrombin so that the thrombin coats the walls of the hole it is creating as the lateral member is pushed through the tissue. As the inner half of the lateral member with the fibrinogen coating enters the insertion hole, it also solvates and mixes with the thrombin which was deposited there as the outer portion of the lateral member passed therethrough, causing the glue formation 64 made up of the mixing of the thrombin and fibrinogen, as seen in FIG. 5A, to become activated and adhering the suture assembly in place Other dual-mixable adhesives can be utilized instead of fibrinogen and thrombin; and the fibrinogen and thrombin, if used, can be deposited alternatively on the inner or outer sides of the lateral member or can be alternatively disposed thereon in segments. Further, such adhesive components can be coated in the same manner onto the thread member so that as it passes through the tissue, it leaves first one adhesive component which is then mixed with the second, thereby activating the adhesive to aid in holding the suture assembly in place. Although FIG. 5 illustrates a single, straight suture member, it should be noted that the suture member of FIG. 5 can also be curved or bent in various directions to supply a single subcutaneous "stitch." The structure of the suture member in some embodiments can be hollow and contain medicine or even arterial stem cells to help reestablish a new blood supply.

Figure 6:
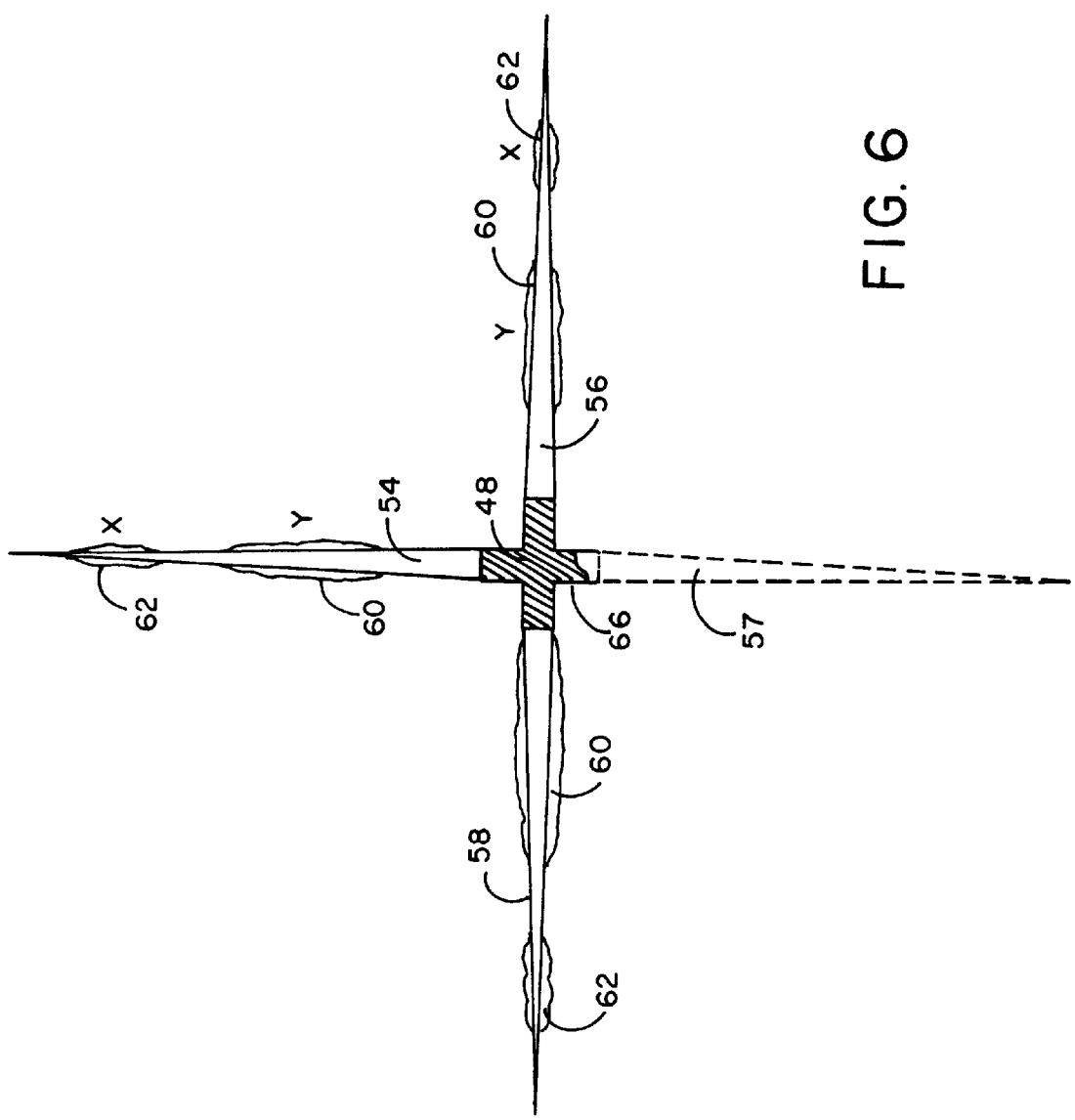
FIG. 6 illustrates a perspective view of a suture member with multiple angular members having an adhesive coating to be held in place with such adhesive.

FIG. 6 illustrates an alternate embodiment of this invention wherein a plurality of lateral members extend from a central junction. Seen in this view are first, second and third multiple lateral members 54, 56 and 58, respectively, each of which extend from central junction 48. It should be noted that although three multiple lateral members are illustrated, more than three could extend from the same central junction. In this view lateral member 57 has been cut off, leaving a stub 66 so that the structure has three usable lateral members which members can, in other embodiments, be disposed at any angle to one another. Such structures are useful in retaining the sides of jagged cuts and can be fitted as needed by cutting off unneeded lateral members. In some instances the suture assembly of this invention can be utilized to secure soft tissue structure to bone. In such cases drill holes can be made in the bone sufficient to allow passage of the needle and thread members of this invention to be drawn therethrough and to pull the lateral member therein. In some cases there is a need to allow for movement of the body part during healing so that the suture assembly can be made of appropriate materials to provide for sufficient flexibility and elasticity, especially when reattaching soft tissue, such as tendons and ligaments, to bone. Appropriate resorbable materials are known for this purpose that work well as suture anchors and that do not leave much remnant suture material which would otherwise weaken the structure. Another useful application for the device of this invention is in the field of hernia repair. Presently preformed mesh has been utilized for hernia repair. Some members of the mesh can be extended as lateral members of this invention from a central body member with a mesh disposed adjacent to the central body member. The lateral members can extend beyond the mesh for installation, as described above, into the body tissue with the needle and thread members attached from the ends of the lateral members adapted to pull and help retain the structure in place to repair the hernia.

Although the present invention has been described with reference to particular embodiments, it will be apparent to those skilled in the art that variations and modifications can be substituted therefor without departing from the principles and spirit of the invention.

I claim:

1. A suture assembly for lateral insertion in body tissue, said body tissue having a cut defined therein, said cut having a length and having first and second opposite sides, said suture assembly for joining said first and second sides of said cut at a junction formed along the length of said cut, comprising:

an elongated central body member having first and second sides and first and second ends;

a plurality of lateral members each having a length, an inner end and an outer end, said lateral members disposed substantially perpendicular to said central body member, and with said lateral members' inner ends attached along said first and second sides of said central body member, said lateral members being substantially parallel to and in planar relation with one another, each lateral member adapted for insertion into a side of said cut;

means for retaining said lateral members in said body tissue;

a plurality of needle members, each having a pointed end and a shank end; and a plurality of thread members, each associated with one of said plurality of needle members, each thread member having a first and a second end, said second end attached to said shank end of its respective needle member and its first end attached to said outer end of its respective lateral member, said needle members for pulling said thread members and attached lateral members through said body tissue on said opposite sides of said cut to position said central body member in said cut and retain said cut in a closed position by said means for retaining said lateral members in said body tissue.

2. The structure of claim 1 wherein said means to retain said plurality of lateral members in said body tissue is an adhesive disposed on said lateral members.

3. The structure of claim 2 wherein said adhesive is a two-part adhesive disposed on said lateral members such that said two-part adhesive mixes when said lateral members are inserted into the sides of said cut, thereby activating said two-part adhesive.

4. The structure of claim 1 wherein said means to retain said lateral members in said tissue comprises a plurality of barb member positioned on said lateral members, each extending at an acute angle to its associated lateral member, said barb members preventing outward movement of said body tissue surrounding said lateral members away from said central body member after said lateral insertion of said lateral members into said first and second sides of said cut and positioning said central body member at said junction of said first and second sides of said cut.

5. The method of joining along a junction the first and second opposite sides of a cut defined in body tissue, comprising the steps of:

providing a suture assembly made of bioabsorbable material having a central body member having two opposite sides, at least two lateral members attached to said central body member one on each opposite side, said lateral members each having an inner end and an outer end and means to retain said lateral members in said body tissue;

providing a thread member and an attached needle member to each lateral member at said outer end of each of said lateral members;

laterally inserting each of said needle members, respectively into an opposite side of said cut;

directing each of said needle members attached to said thread members to a respective point of exit out of said body tissue;

pulling said lateral members positioned along said sides of said central body member into said opposite sides of said cut by pulling on said needle members and drawing said thread members through said body tissue on said opposite sides of said cut by pulling said lateral members into said body tissue;

engaging said body tissue of said first and second sides of said cut by said means to retain said lateral members in said body tissue;

preventing outward movement of said first and second sides of said cut away from said central body member by said means to retain said lateral members in said body tissue of said first and second sides of said cut;

holding said cut closed around said central body member by said engagement of said means to retain said later members in said body tissue; and cutting said thread members at said respective points of exit.

6. The method of joining body tissue at first and second sides of a cut defined in body tissue, comprising the steps of:

providing a suture assembly having a central junction and at least two lateral members attached to said central junction;

positioning a two-part adhesive on said lateral members;

inserting said lateral members into said body tissue;

mixing said two-part adhesive by contact with said body tissue as said lateral members are inserted;

activating said two-part adhesive by said mixing; and retaining said lateral members in said body tissue by said activated two-part adhesive.

7. The method of claim 6 further including the steps of:

providing barb members on at least one lateral member; and retaining said lateral members in said body tissue by said barb members and said two-part adhesive.

* * * * *